(12) United States Patent
Ono et al.

(10) Patent No.: US 8,382,679 B2
(45) Date of Patent: Feb. 26, 2013

(54) AUTONOMIC NERVE ACTIVITY MEASURING APPARATUS AND AUTONOMIC NERVE ACTIVITY MEASURING METHOD

(75) Inventors: Yoshinobu Ono, Tokyo (JP); Takeshi Kojima, Tokyo (JP); Ryousuke Ushijima, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 536 days.

(21) Appl. No.: 12/362,736

(22) Filed: Jan. 30, 2009

(65) Prior Publication Data

US 2009/0198147 A1 Aug. 6, 2009

(30) Foreign Application Priority Data

Jan. 31, 2008 (JP) ................................. 2008-021997

(51) Int. Cl.
*A61B 5/00* (2006.01)
(52) U.S. Cl. ........................................ 600/554; 600/500
(58) Field of Classification Search .................. 600/301, 600/372, 485, 501, 554, 500
See application file for complete search history.

(56) References Cited

U.S. PATENT DOCUMENTS

| | | | | |
|---|---|---|---|---|
| 2003/0125631 A1* | 7/2003 | Amano | .......... | 600/500 |
| 2006/0149152 A1* | 7/2006 | Amitzur et al. | .......... | 600/485 |
| 2006/0270944 A1* | 11/2006 | King | .......... | 600/554 |
| 2007/0021673 A1* | 1/2007 | Arbel et al. | .......... | 600/500 |

FOREIGN PATENT DOCUMENTS

| | | |
|---|---|---|
| EP | 1224951 A1 | 7/2002 |
| JP | 7-313494 A | 12/1995 |
| JP | 11-299740 A | 11/1999 |
| JP | 2003-339651 A | 12/2003 |
| JP | 2004-351184 A | 12/2004 |
| JP | 2004-358022 A | 12/2004 |
| JP | 2005-329148 A | 12/2005 |
| JP | 2006-516000 A | 6/2006 |
| JP | 2007-061572 A | 3/2007 |
| JP | 2007-97678 A | 4/2007 |
| WO | 2007/013326 A1 | 2/2007 |

OTHER PUBLICATIONS

European Office Action issued Jul. 2, 2010 in corresponding European Application No. 09 001 352.5.
Extended European Search Report dated Apr. 6, 2009.
Office Action drafted Jun. 14, 2012 by the Japanese Patent Office in counterpart Japanese Application No. 2008-021997.

* cited by examiner

*Primary Examiner* — Max Hindenburg
(74) *Attorney, Agent, or Firm* — Sughrue Mion, PLLC

(57) ABSTRACT

An autonomic nerve activity measuring apparatus includes: a pulse wave acquiring unit, configured to acquire at least two pulse wave signals from a living body; an electric stimulation unit, configured to apply electric stimulation to the living body; a comparison unit, configured to compare the pulse wave signals acquired by the pulse wave acquiring unit; and an analysis unit, configured to analyze comparison result provided by the comparison unit.

22 Claims, 8 Drawing Sheets

AUTONOMIC NERVE ACTIVITY MEASURING APPARATUS AND AUTONOMIC NERVE ACTIVITY MEASURING METHOD

BACKGROUND OF THE INVENTION

This invention relates to an autonomic nerve activity measuring apparatus and an autonomic nerve activity measuring method for applying electric stimulation to a living body and measuring autonomic nerve activity from a pulse wave signal reflecting the constriction of a peripheral blood vessel by an autonomic nerve (sympathetic nerve and parasympathetic nerve).

A skin blood volume, an electrocardiogram waveform, etc., is representative biological information to measure the autonomic nervous system and an attempt has been made to evaluate the state of the autonomic nervous and the balance and the functionality as to which of the sympathetic nerve and the parasympathetic nerve is dominant from the heart rate and the blood pressure and frequency analysis and chaos analysis of the digital pulse volume and further pulse wave acceleration of the digital pulse volume, etc.

For example, there are a related art of evaluating the autonomic nerve function from the a-a (systolic early positive wave) time pulse wave acceleration (refer to JP-A-2004-358022), and a related art of measuring a pulse wave for about 20 seconds and determining autonomic nerve imbalance from a distribution of peak and bottom times for each beat (refer to JP-A-2007-61572, particularly "embodiment 2").

However, although qualitative evaluation and analysis of the autonomic nerve can be conducted, disturbance of the visual sense, the acoustic sense, the smell sense, etc., has an effect on evaluating of the autonomic nerve and it is difficult to selectively evaluate the function of the sympathetic nerve and the function of the parasympathetic nerve.

Generally, if the measuring time is short, information required for diagnosis is insufficient and an error becomes large On the other hand, considering that heart rate fluctuation has periodicity, if the measuring time is simply prolonged, the effect of the disturbance is easily received and it cannot be said that the prolonged measuring time is advantageous. That is, to conduct autonomic nerve activity measurement with no error, how long the measuring time is to be set cannot quantitatively be determined.

With the circumstances as described above as the background, an objective diagnosis of the state of the autonomic nerve is conducted by applying stimulation by an acoustic signal and an image signal and keeping track of the response time and the restoration potential of the autonomic nerve from fluctuation of vital sign (Refer to JP-A-2005-329148, particularly 0033). However, a problem remains in that the diagnosis can be applied only to a person having a normal audio visual function, and under the present circumstances, there is a demand for realizing an apparatus and a method for performing excellent autonomic nerve activity measurement.

Further, generally inspiration in respiration of a living body derives from the sympathetic nerve and expiration derives from the parasympathetic nerve. Therefore, the expiration becomes a disturbance factor of sympathetic nerve measurement from the relation between the respiration and the sympathetic nerve.

SUMMARY

It is therefore an object of the invention to provide an autonomic nerve activity measuring apparatus and measuring method capable of conducting autonomic nerve activity measuring more than was previously possible.

It is another object of the invention to provide an apparatus and a method capable of excluding disturbance deriving from respiration and determining the nature inspection of a sympathetic nerve.

In order to achieve the object, according to the invention, there is provided an autonomic nerve activity measuring apparatus comprising:
a pulse wave acquiring unit, configured to acquire at least two pulse wave signals from a living body;
an electric stimulation unit, configured to apply electric stimulation to the living body;
a comparison unit, configured to compare the pulse wave signals acquired by the pulse wave acquiring unit; and
an analysis unit, configured to analyze comparison result provided by the comparison unit.

The comparison unit may compare the pulse wave signals acquired by the pulse wave acquiring unit before and after the electric stimulation is applied to the living body.

The electric stimulation may include a first electric stimulation and a second electric stimulation which are different from each other in intensity. The comparison unit may compare the pulse wave signals acquired by the pulse wave acquiring unit when the first electric stimulation and the second electric stimulation are applied to the living body.

The first electric stimulation may have low intensity that the living body does not feel. The second electric stimulation may have high intensity that the living body feels.

The pulse wave signal may be at least one of amplitude of a P wave, amplitude of a T wave, amplitude of a D wave, amplitude of pulse wave velocity, amplitude of pulse wave acceleration, a pulse wave amplitude ratio, a pulse wave velocity amplitude ratio, a pulse wave acceleration amplitude ratio, a power fluctuation pattern of each wavelength provided by pulse wave frequency analysis, and an elastic coefficient.

The pulse wave amplitude ratio may include the ratio between the P wave and the D wave.

The pulse wave acceleration amplitude ratio may include the ratio between a b wave and a d wave.

The autonomic nerve activity measuring apparatus may further include a respiration detection unit, configured to detect a respiration signal from the living body. The electric stimulation unit may apply the electric stimulation to the living body in response to the detected respiration signal.

The respiration detection unit may detect the respiration signal by using one of an airway flow sensor, a thermistor sensor, an airway pressure sensor, a carbon dioxide concentration sensor, an impedance sensor, and a photoplethysmographic sensor.

The respiration signal may include at least one of expiration and inspiration.

The electric stimulation unit may apply the electric stimulation to the living body in either an expiratory phase or an inspiratory phase.

In order to achieve the object, according to the invention, there is also provided a method of measuring autonomic nerve activity of a living body, the method comprising:
acquiring at least two pulse wave signals from the living body;
applying electric stimulation to the living body;
comparing the acquired pulse wave signals; and
analyzing comparison result.

The pulse wave signals, which are acquired before and after the electric stimulation is applied to the living body, may be compared.

The electric stimulation may include a first electric stimulation and a second electric stimulation which are different from each other in intensity. The pulse wave signals, which are acquired when the first electric stimulation and the second electric stimulation are applied to the living body, may be compared.

The first electric stimulation may have low intensity that the living body does not feel. The second electric stimulation may have high intensity that the living body feels.

The pulse wave signal may be at least one of amplitude of a P wave, amplitude of a T wave, amplitude of a D wave, amplitude of pulse wave velocity, amplitude of pulse wave acceleration, a pulse wave amplitude ratio, a pulse wave velocity amplitude ratio, a pulse wave acceleration amplitude ratio, a power fluctuation pattern of each wavelength provided by pulse wave frequency analysis, and an elastic coefficient.

The pulse wave amplitude ratio may include the ratio between the P wave and the D wave.

The pulse wave acceleration amplitude ratio may include the ratio between a b wave and a d wave.

The method may further include detecting a respiration signal from the living body. The electric stimulation may be applied to the living body in response to the detected respiration signal.

The respiration signal may be detected by using one of an airway flow sensor, a thermistor sensor, an airway pressure sensor, a carbon dioxide concentration sensor, an impedance sensor, and a photoplethysmographic sensor.

The respiration signal may include at least one of expiration and inspiration.

The electric stimulation may be applied to the living body in either an expiratory phase or an inspiratory phase.

DETAILED DESCRIPTION OF PREFERRED EMBODIMENTS

Figure 1:
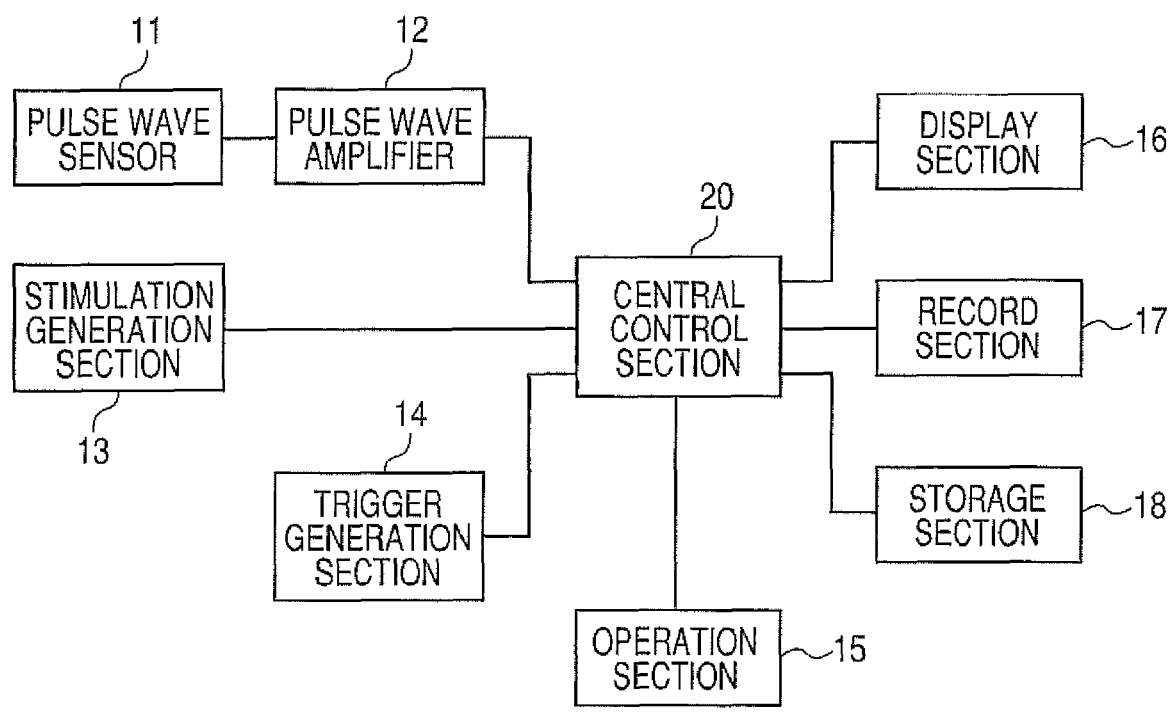
FIG. 1 is a block diagram of an embodiment of an autonomic nerve activity measuring apparatus according to the present invention.

An embodiment of an autonomic nerve activity measuring apparatus and an autonomic nerve activity measuring method according to the invention will be discussed with reference to the accompanying drawings. FIG. 1 is a block diagram of the embodiment of the autonomic nerve activity measuring apparatus. A pulse wave signal is obtained using a pulse wave sensor 11 and is amplified by a pulse wave amplifier 12 according to a predetermined gain and then is fed into a central control section 20. A sensor including a light receiving element and a right transmitting element disclosed in JP-A-2001-78990 or the like can be used as the pulse wave sensor 11.

The pulse wave sensor 11 and the pulse wave amplifier 12 are a pulse wave acquiring unit for acquiring a pulse wave signal from a living body. The pulse wave acquiring unit may be capable of measuring at least one or more of photoplethysmograph, pressure pulse wave, blood flow, and blood pressure.

A stimulation generation section 13 containing an electrode put on a living body and a trigger generation section 14 are connected to the central control section 20. The stimulation generation section 13 and the trigger generation section 14 may make up an electric stimulation unit for applying electric stimulation to a living body by predetermined operation. As electric stimulation is generated from the stimulation generation section 13, the trigger generation section 14 generates a trigger signal and sends the trigger signal to the central control section 20.

An operation section 15 is connected to the central control section 20. The operation section 15 may be provided with keys, etc., for enabling the user to set a voltage value, a frequency, etc., to be generated from the stimulation generation section 13. The keys and the trigger generation section 14 may be connected to the stimulation generation section 13 to make up an electric stimulation unit. The operation section 15 is also provided with keys for entering a command, data, etc., given to the central control section 20.

The central control section 20 is implemented as a CPU, etc., and has a comparison unit for making a comparison using a pulse wave signal acquired by the pulse wave acquiring unit and the trigger signal and an analysis unit for analyzing the comparison result.

A display section 16 of an LCD, etc., a record section 17 of a printer, etc., and a storage section 18 made up of various memory devices are connected to the central control section 20. The display section 16 and the record section 17 output the analysis result, etc., of the comparison unit and the analysis unit included in the central control section 20. Particularly, they make up an output unit for obtaining and outputting the result of comparison and analysis of pulse wave signals acquired before and after electric stimulation based on a trigger signal is applied and the result of comparison and analysis of pulse wave signals acquired when different intensity electric stimulations are applied. The acquired pulse waves, result, and the like are stored in the storage section 18. The expression "before and after electric stimulation based on a trigger signal" contains the case where the electric stimulation unit does not apply stimulation; if the electric stimulation unit applies stimulation, the expression contains obtaining the separate analysis results before and after the stimulation. It further contains obtaining the result across the time intervals before and after the stimulation containing the timing at which simulation is applied by the electric stimulation unit.

Computation of the comparison unit and the analysis unit will be discussed. The pulse wave signal is a generic name for signals deriving from pulse waves described below. Specifically, the pulse wave signal is any one or more of the amplitude of a P wave, the amplitude of a T wave, the amplitude of a D wave, the amplitude of pulse wave velocity, the amplitude of pulse wave acceleration, a pulse wave amplitude ratio, a pulse wave velocity amplitude ratio, a pulse wave acceleration amplitude ratio, a power fluctuation pattern of each wavelength provided by pulse wave frequency analysis, and an elastic coefficient.

Figure 2A:
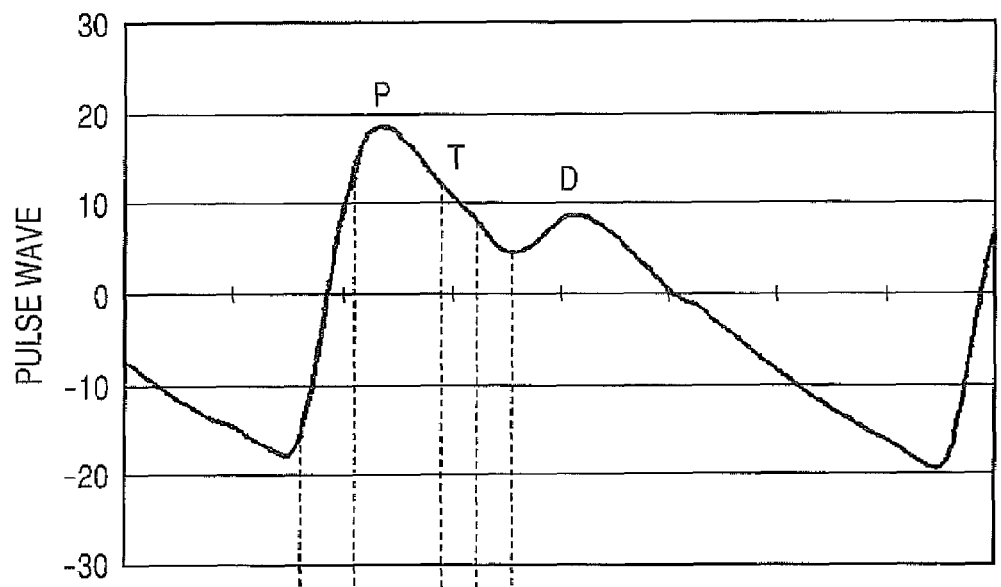
FIGS. 2A and 2B are drawings to describe the names of parts in a pulse wave and pulse wave acceleration, respectively.

A one-period pulse wave is as shown in FIG. 2A. First derivative of the pulse wave is computed to provide a pulse wave velocity and further second derivative is computed by the comparison unit to provide pulse wave acceleration shown in FIG. 2B. The first peak in the one-period pulse wave is P wave called Percussion wave. The second peak in the one-period pulse wave is T wave called Tidal wave. The third peak in the one-period pulse wave is D wave called Dicrotic wave. The elastic coefficient is the height ratio between the two waves of the Percussion wave (P wave) and the Tidal wave (T wave).

The comparison unit performs computation for obtaining trends of the P wave and the D wave and also trends of pulse wave amplitude ratios containing the ratio between the P wave and the D wave (P/D and D/P).

Figure 2B:
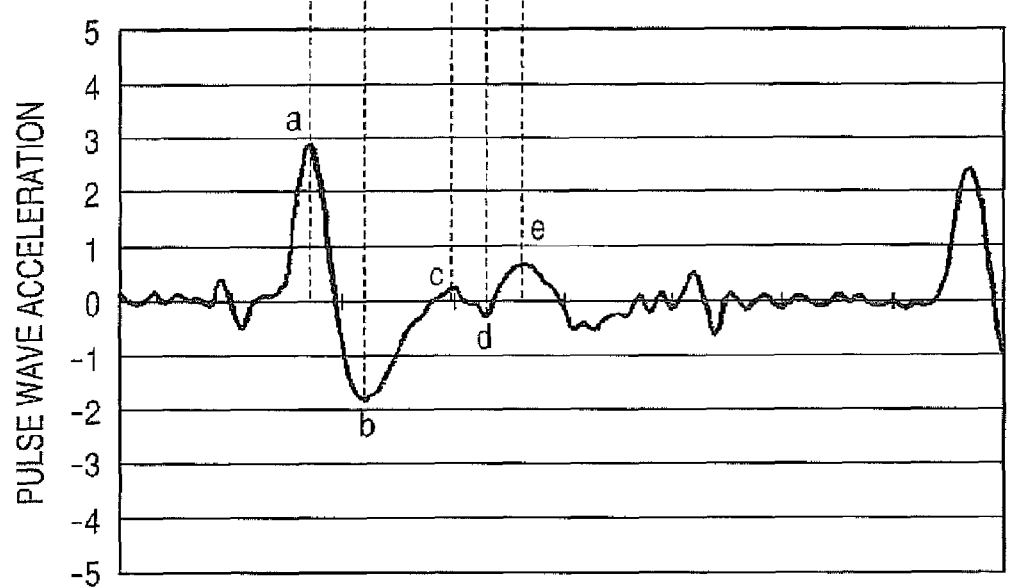

As another example, in the pulse wave acceleration shown in FIG. 2B, a positive wave having the first local maximum point is called a wave (systolic early positive wave) and a negative wave following the a wave is called b wave (systolic early negative wave), followed by c wave (systolic medium re-ascending wave), d wave (systolic late re-descending wave), and e wave (diastolic early positive wave). The comparison unit may perform computation for obtaining trends of b/a, c/a, d/a, e/a, and b/d as pulse wave acceleration amplitude ratios.

As still another example, the comparison unit may perform frequency resolution relative to the pulse wave and may perform computation for making a histogram with the frequency as an axis.

Each of the computations described above is also performed before and after stimulation of the electric stimulation unit and when different stimulation is applied, thereby finding the pulse wave signal comparison results such as a trend curve of pulse wave amplitude ratio (P/D, D/P), a trend curve of pulse wave acceleration amplitude ratio (b/a, c/a, d/a, e/a, b/d), and a pulse wave frequency component distribution. Further, the analysis unit evaluates the nature inspection of the sympathetic nerve according to change appearing in the pulse wave signal caused by the presence or absence of stimulation and the stimulation intensity difference based on the comparison results. The evaluation result may be output from the display section 16 and the record section 17.

Figure 3A:
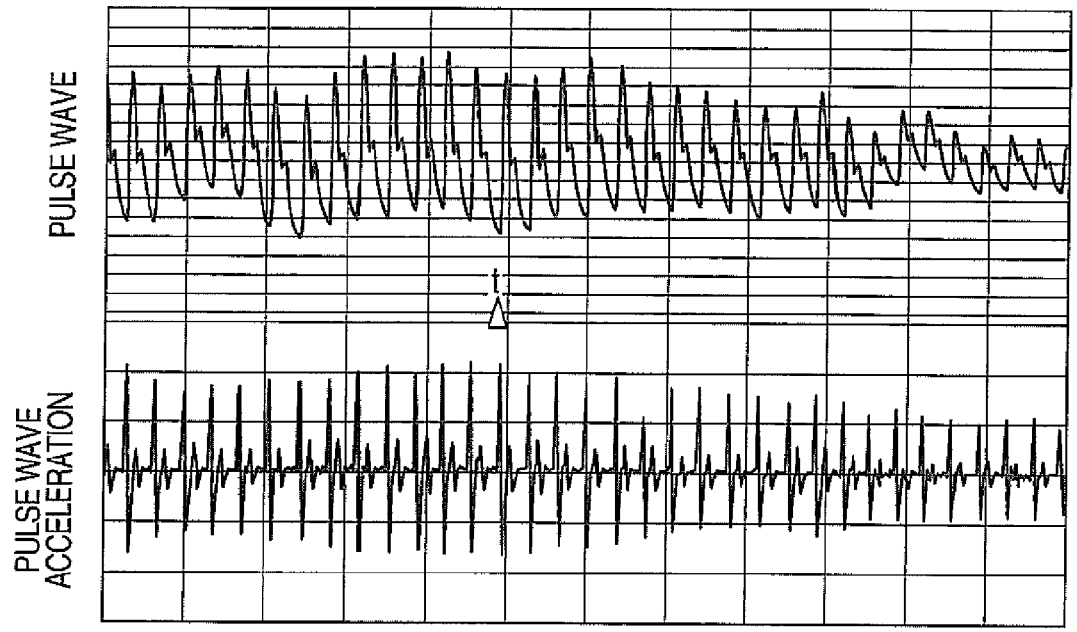
FIGS. 3A and 3B are drawings to show trends of pulse waves and pulse wave acceleration provided by the embodiment of the autonomic nerve activity measuring apparatus according to the invention.
Figure 3B:
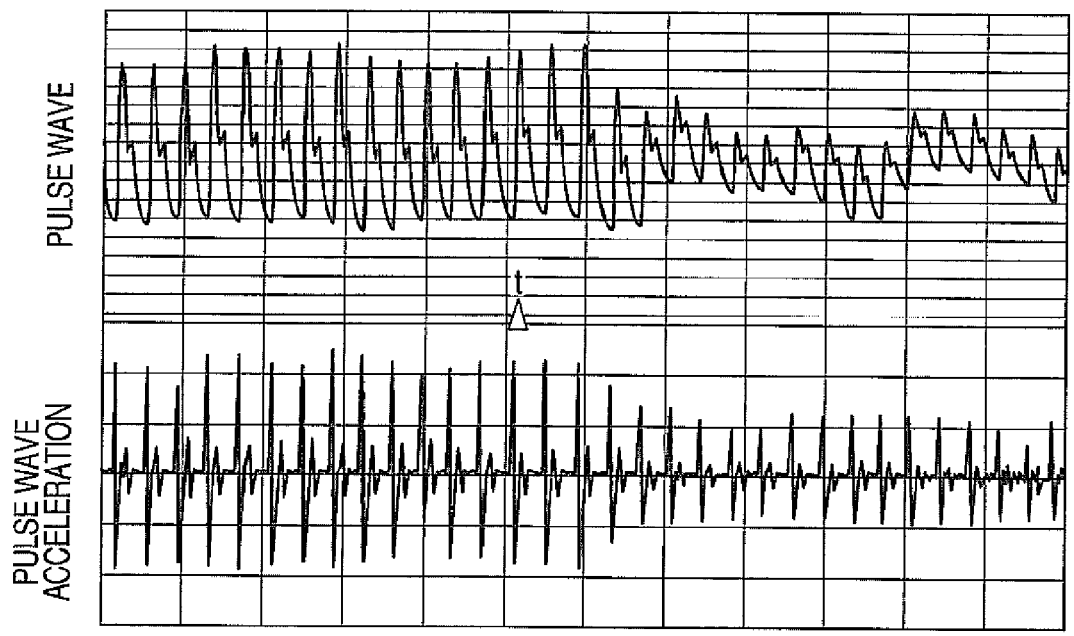

The measuring result of the apparatus of the embodiment is shown. FIG. 3A shows pulse wave and pulse wave acceleration when the electric stimulation unit applies electric stimulation of extremely low intensity that a living body does not feel (the intensity may be zero), and FIG. 3B shows pulse wave and pulse wave acceleration when the electric stimulation unit applies electric stimulation of high intensity that a living body feels (here, 0.4-mA square-wave current with duration of 0.5 ms is used and five train stimulations are applied at 5.0-ms intervals); a trigger signal applies stimulation at time t. It is seen from FIG. 3A that the sympathetic nerve scarcely responds to the electric stimulation of low intensity and no change occurs in the pulse wave. On the other hand, it is seen from FIG. 3B that the sympathetic nerve responds to the electric stimulation of high intensity, constriction of a peripheral blood vessel occurs, and change occurs in the waveforms of the pulse wave and the acceleration pulse wave.

Figure 4:
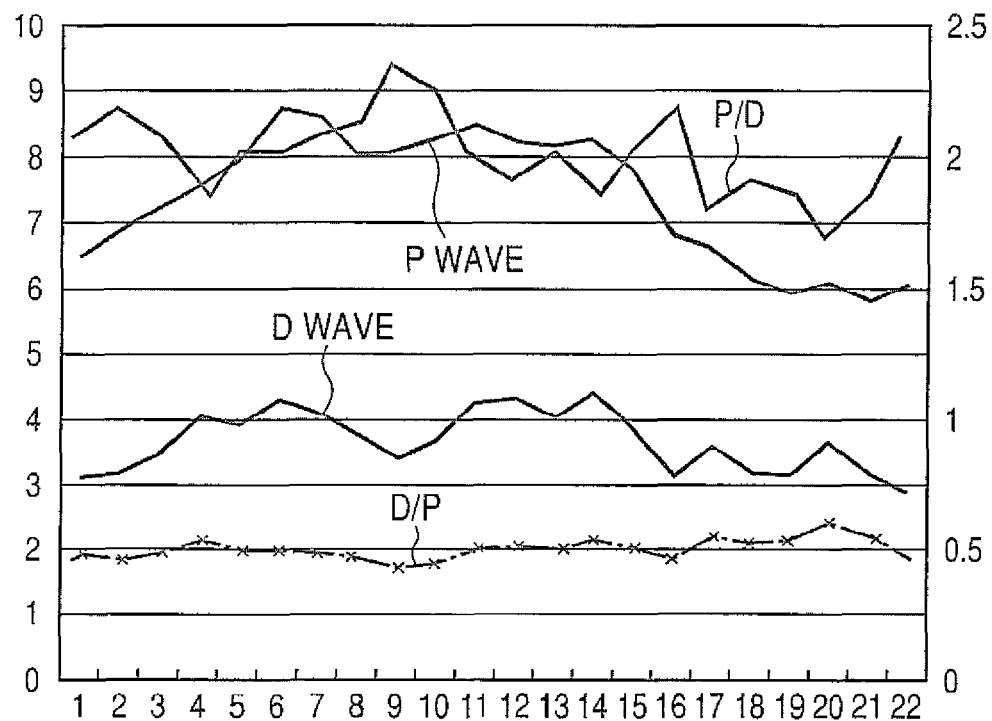
FIG. 4 is a drawing to show pulse wave amplitude ratio trends of a normal person with no electric stimulation, provided by the embodiment of the autonomic nerve activity measuring apparatus according to the invention.
Figure 5:
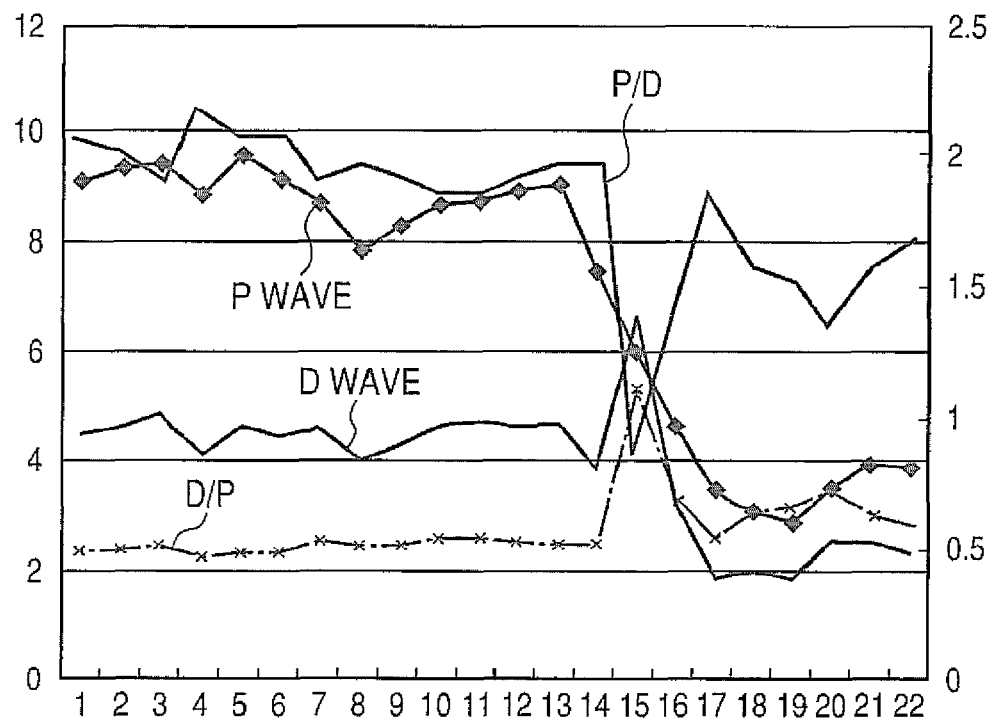
FIG. 5 is a drawing to show pulse wave amplitude ratio trends of the normal person with electric stimulation applied at the 11th pulse, provided by the embodiment of the autonomic nerve activity measuring apparatus according to the invention.
Figure 6:
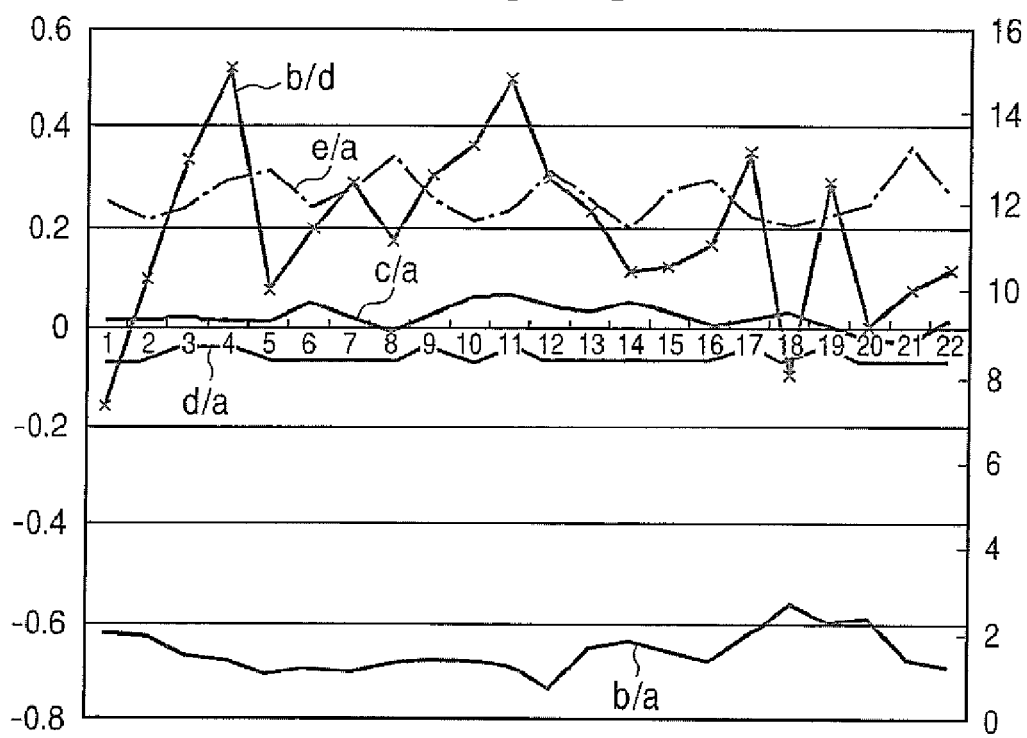
FIG. 6 is a drawing to show acceleration pulse wave amplitude ratio trends of the normal person with no electric stimulation, provided by the embodiment of the autonomic nerve activity measuring apparatus according to the invention.
Figure 7:
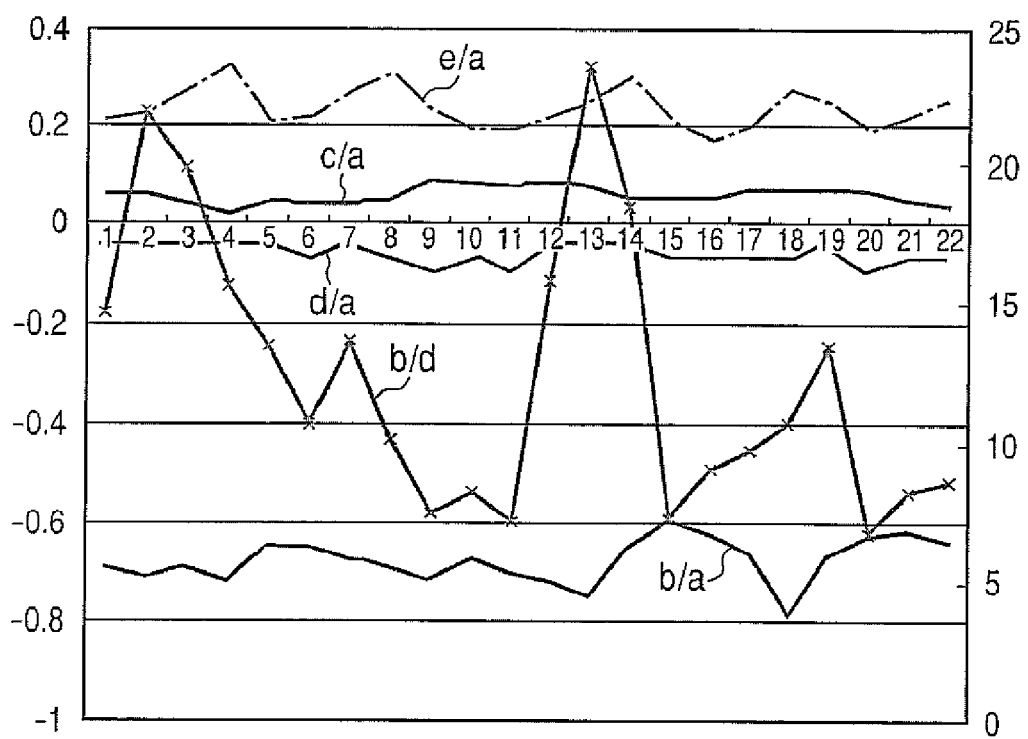
FIG. 7 is a drawing to show acceleration pulse wave amplitude ratio trends of the normal person with electric stimulation applied at the 11th pulse, provided by the embodiment of the autonomic nerve activity measuring apparatus according to the invention.

Further, FIGS. 4 to 7 show the measuring result of the apparatus of the embodiment. FIG. 4 shows pulse wave amplitude trends of a normal subject when the electric stimulation unit applies stimulation of low intensity. FIG. 5 shows pulse wave amplitude trends of the normal subject when the electric stimulation unit applies stimulation of high intensity. FIG. 6 shows acceleration pulse wave amplitude trends of a normal subject when the electric stimulation unit applies stimulation of low intensity. FIG. 7 shows pulse wave acceleration amplitude trends of the normal subject when the electric stimulation unit applies stimulation of high intensity. The horizontal axis indicates what number pulse each pulse of the pulse wave is, the left vertical axis indicates the amplitude value, and the right vertical axis indicates the amplitude ratio value. In this example, it is obvious from FIG. 5 that if electric stimulation of high intensity that a living body feels is applied at the 11th pulse, large change occurs at the 14th pulse. This means that response to applying electric stimulation is noticeable according to the computation result of the embodiment providing the ratio. Likewise, it can be acknowledged in FIG. 7 that noticeable change is measured in the ratio between the b and d waves in the acceleration pulse wave.

Figure 8:
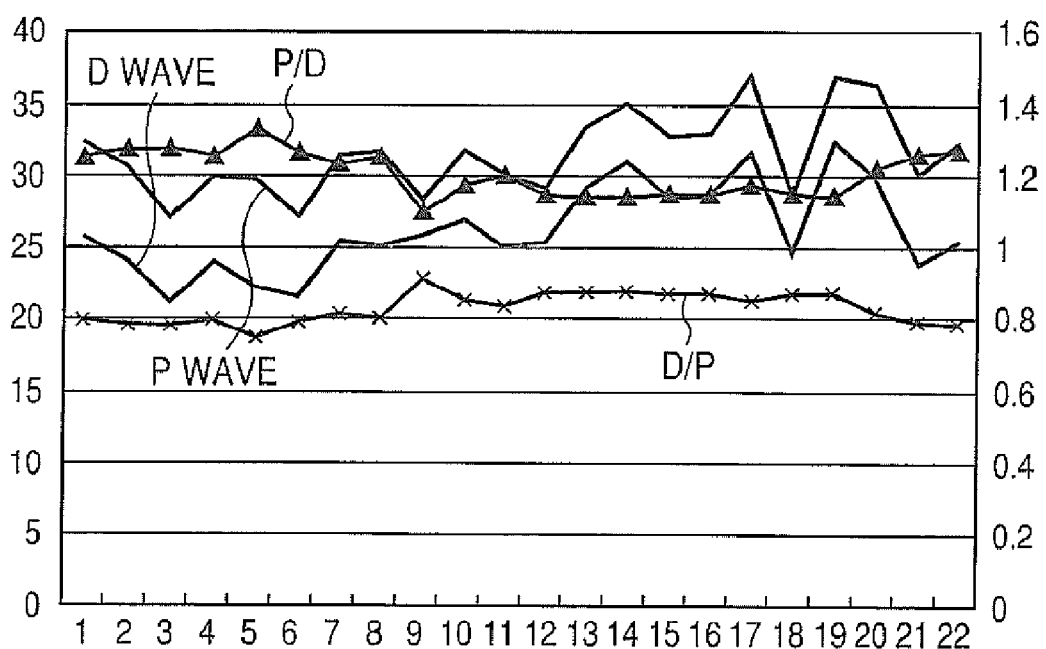
FIG. 8 is a drawing to show pulse wave amplitude ratio trends of an abnormal person with electric stimulation applied at the 11th pulse, provided by the embodiment of the autonomic nerve activity measuring apparatus according to the invention.
Figure 9:
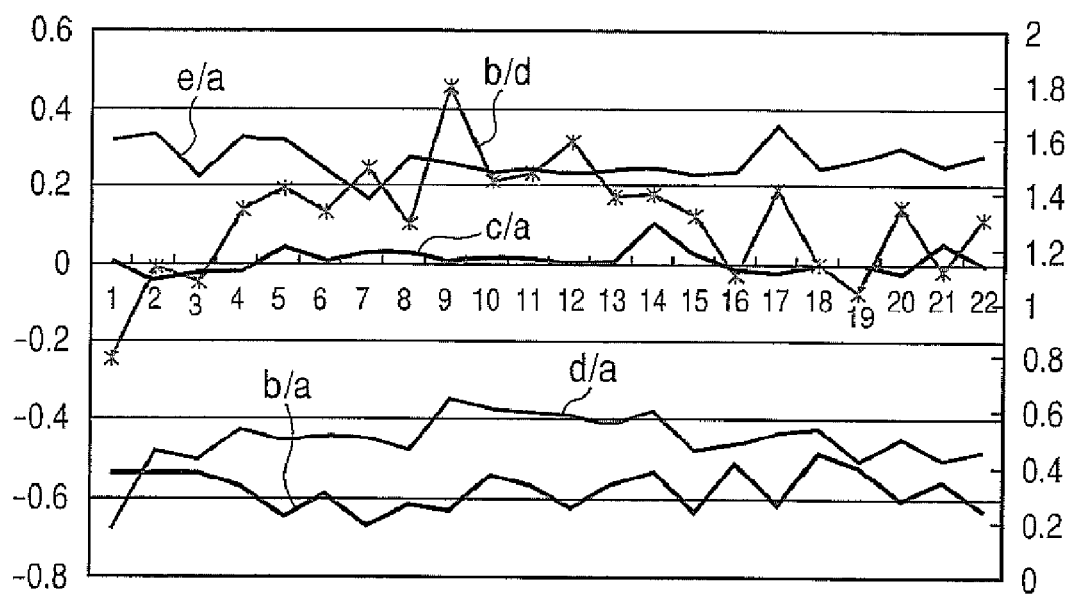
FIG. 9 is a drawing to show acceleration pulse wave amplitude ratio trends of the abnormal person with electric stimulation applied at the 11th pulse, provided by the embodiment of the autonomic nerve activity measuring apparatus according to the invention.

Further, FIGS. 8 and 9 show the measuring result of the apparatus of the embodiment. FIG. 8 shows pulse wave amplitude trends of an abnormal subject as for the autonomic nerve (simply, abnormal person) when the electric stimulation unit applies stimulation of high intensity. FIG. 9 shows acceleration pulse wave amplitude trends of the abnormal subject when the electric stimulation unit applies stimulation of high intensity.

FIG. 8 corresponds to FIG. 5, and FIG. 9 corresponds to FIG. 7. Although the same electric stimulation as the normal person is applied at the 11th pulse, change is not observed in the pulse wave or the acceleration pulse wave of the abnormal person after the electric stimulation, and the computation result is in large contrast with the computation result for the pulse wave of the normal person wherein change occurs at the 14th pulse. That is, it is considered that a nerve impulse caused by pain responsive to the electric stimulation is induced and the sympathetic nerve state as the reflection is measured, and the advantage of making it possible to easily measure abnormal response of the sympathetic nerve can be provided.

Figure 10:
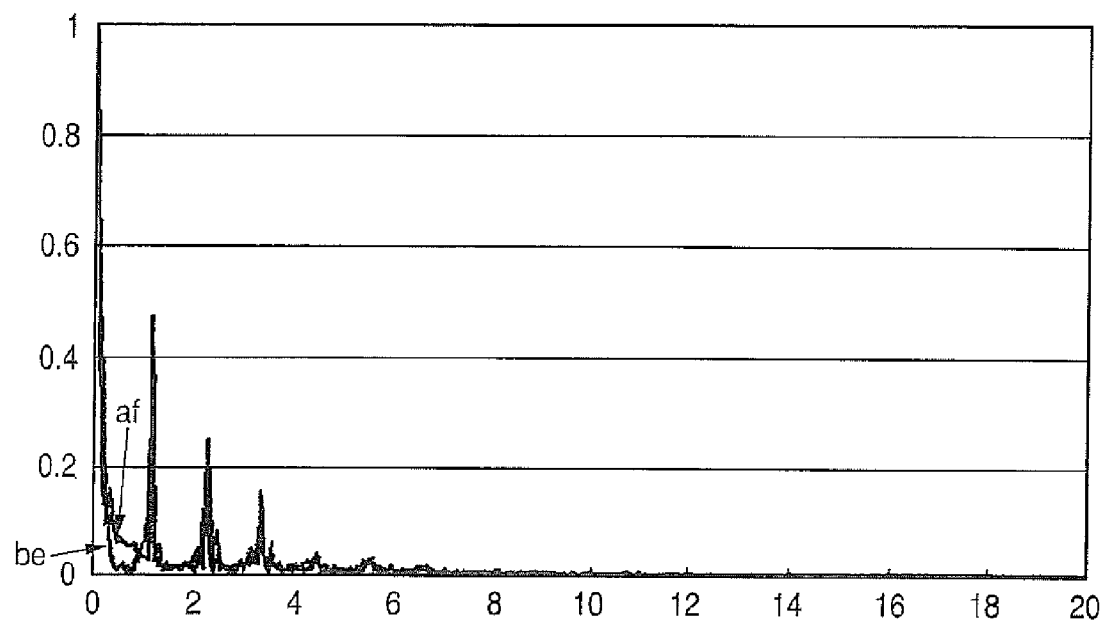
FIG. 10 is a drawing to show a frequency distribution of a normal subject before and after the 14th pulse when an electric stimulation unit does not apply electric stimulation, provided by the embodiment of the autonomic nerve activity measuring apparatus according to the invention.
Figure 11:
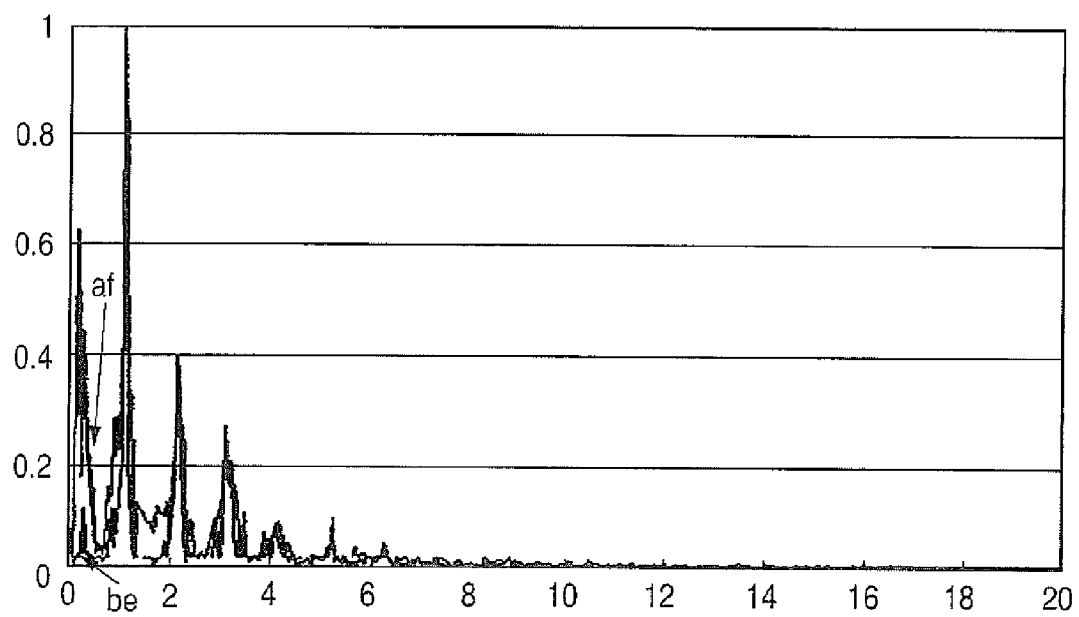
FIG. 11 is a drawing to show a frequency distribution of the normal subject before and after the 14th pulse when the electric stimulation unit applies electric stimulation, provided by the embodiment of the autonomic nerve activity measuring apparatus according to the invention.
Figure 12:
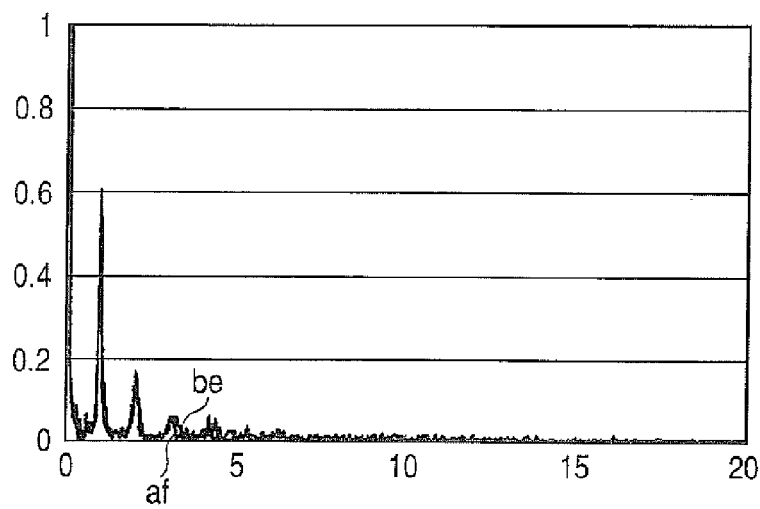
FIG. 12 is a drawing to show a frequency distribution of the abnormal subject before and after the 14th pulse when the electric stimulation unit applies electric stimulation, provided by the embodiment of the autonomic nerve activity measuring apparatus according to the invention.

FIGS. 10 to 12 show the measuring result of the apparatus of the embodiment. FIG. 10 shows a frequency distribution of the normal subject before and after the 11th pulse when the electric stimulation unit applies electric stimulation of extremely low intensity that a living body does not feel. Frequency is taken on the horizontal axis, and power is taken on the vertical axis. From the result, it is seen that a frequency distribution be forming the pulse wave before the 11th pulse and a frequency distribution af forming the pulse wave after the 11th pulse scarcely differ in pulse wave signal.

FIG. 11 shows a frequency distribution of the normal subject before and after the 11th pulse when the electric stimulation unit applies electric stimulation that a living body feels. Frequency is taken on the horizontal axis, and power is taken on the vertical axis. From the result, it is seen that the arterial volume decreases because of constriction of a peripheral blood vessel and a low frequency component increases in the frequency distribution af forming the pulse wave after the 11th pulse as compared with the frequency distribution be forming the pulse wave before the 11th pulse.

FIG. 12 shows a frequency distribution of the abnormal subject before and after the 11th pulse when the electric stimulation unit applies electric stimulation. Frequency is taken on the horizontal axis, and degree (relative value) is taken on the vertical axis. From the result, it is seen that a frequency distribution be forming the pulse wave before the 11th pulse and a frequency distribution af forming the pulse wave after the 11th pulse scarcely differ although electric stimulation is applied, and it is understood that if high electric stimulation is applied, the sympathetic nerve does not appropriately respond to the electric stimulation and constriction of a peripheral blood vessel does not occur. This means that abnormal response of the sympathetic nerve can be acknowledged.

The embodiment described above can be applied not only to inspection of the nerve function, but also to evaluation of abnormal pain sense caused by diabetes, sympathoplegia caused by Parkinson's disease, etc.

Figure 13:
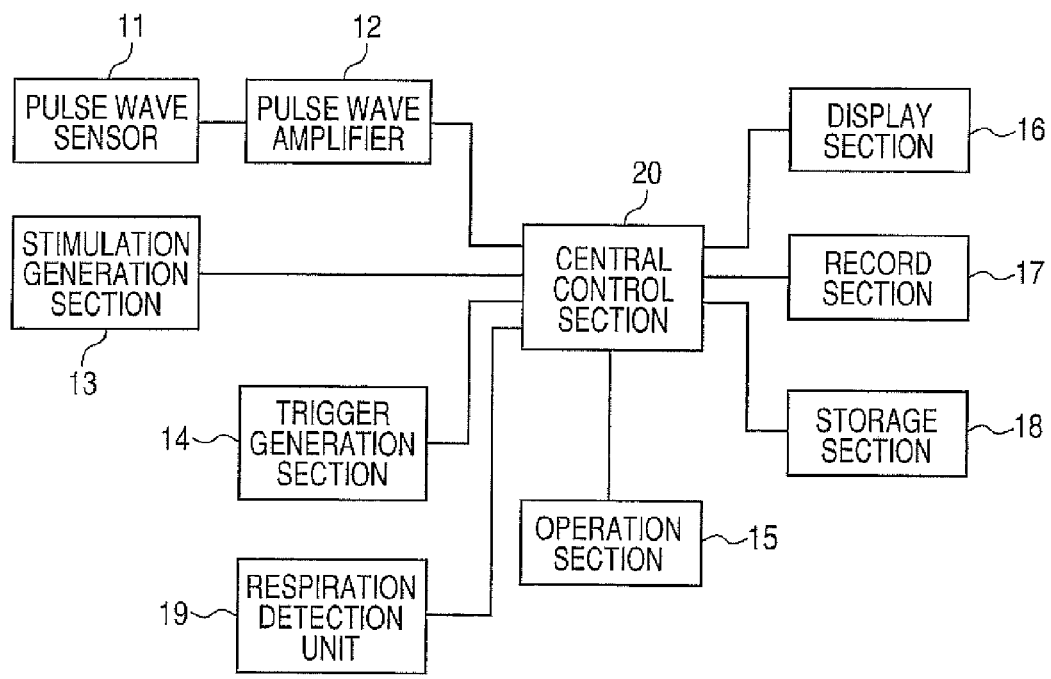
FIG. 13 is a block diagram of an embodiment of an autonomic nerve activity measuring apparatus provided with a mechanism for excluding the effect of disturbance caused by respiration according to the invention.

Further, an embodiment for excluding the effect of disturbance caused by respiration will be discussed with FIG. 13. The configuration differs from that of the embodiment in FIG. 1 only in a respiration detection unit 19. The respiration detection unit 19 contains at least one of an airway flow sensor, a thermistor (temperature) sensor, an airway pressure sensor, a carbon dioxide concentration sensor, an impedance sensor, and a photoplethysmographic sensor.

The respiration detection unit 19 detects an airway (respiration) signal of a living body, for example, expiration and inspiration. When detecting expiration or inspiration, the respiration detection unit 19 sends a notification of detection of expiration or inspiration to a central control section 20. Upon reception of the notification, the central control section 20 instructs an electric stimulation generation section 13 to apply stimulation in an expiratory phase or an inspiratory phase of respiration.

Electric stimulation is applied at the timing of the expiratory phase or the inspiratory phase of respiration, whereby it is made possible to lessen the disturbance factor of sympathetic nerve measuring caused by respiration.

According to an aspect of the invention, a nerve impulse caused by pain responsive to the electric stimulation is induced and the pulse wave signal deriving from constriction of a peripheral blood vessel appearing as the reflection is measured, whereby it is made possible to evaluate the nature inspection of a sympathetic nerve. Further, it is also made possible to easily detect abnormal response of the homeostatic of the sympathetic nerve. Response of a pulse wave signal can be quickly obtained by applying electric stimulation different from a sound or lights Reaction can be displayed distinctly according to the pulse wave amplitude ratio and the pulse wave acceleration amplitude ratio. The range is widened according to the frequency component and the measurement result can be provided for facilitating analysis and evaluation.

The pulse wave amplitude ratio includes the ratio between the P wave and the D wave, and the pulse wave acceleration amplitude ratio includes the ratio between the b wave and the d wave, so that reaction can be displayed distinctly according to the ratios.

It is made possible to exclude the effect of disturbance caused by respiration and evaluate the nature inspection of a sympathetic nerve with high accuracy.

The possibility is also high that the invention may be applied not only to inspection of the nerve function, but also to fields of evaluation of abnormal pain sense caused by diabetes, sympathoplegia caused by Parkinson's disease, etc., and the like.

What is claimed is:

1. An autonomic nerve activity measuring apparatus comprising:
    an electric stimulation unit, configured to apply electric stimulation to a living body, the electric stimulation unit including at least one electrode to be placed on the living body;
    a pulse wave acquiring unit, configured to acquire at least two pulse wave signals from the living body, at least one of the pulse wave signals is derived from constriction of a peripheral blood vessel of the living body due to a nerve impulse induced by the electric stimulation, the pulse wave acquiring unit including a sensor; and
    a computer processor, the computer processor comprising:
        a comparison unit, configured to compare the pulse wave signals acquired by the pulse wave acquiring unit; and
        an analysis unit, configured to determine abnormal response of an autonomic nerve based on a comparison result provided by the comparison unit when no change occurs in the pulse wave signals.

2. The autonomic nerve activity measuring apparatus as claimed in claim 1, wherein
    the comparison unit compares the pulse wave signals acquired by the pulse wave acquiring unit before and after the electric stimulation is applied to the living body.

3. The autonomic nerve activity measuring apparatus as claimed in claim 1, wherein
    the electric stimulation includes a first electric stimulation and a second electric stimulation which are different from each other in intensity, and
    the comparison unit compares the pulse wave signals acquired by the pulse wave acquiring unit when the first electric stimulation and the second electric stimulation are applied to the living body.

4. The autonomic nerve activity measuring apparatus as claimed in claim 3, wherein
the first electric stimulation has low intensity, and
the second electric stimulation has high intensity.

5. The autonomic nerve activity measuring apparatus as claimed in claim 1, wherein
the pulse wave signal is at least one of amplitude of a P wave, amplitude of a T wave, amplitude of a D wave, amplitude of pulse wave velocity, amplitude of pulse wave acceleration, a pulse wave amplitude ratio, a pulse wave velocity amplitude ratio, a pulse wave acceleration amplitude ratio, a power fluctuation pattern of each wavelength provided by pulse wave frequency analysis, and an elastic coefficient.

6. The autonomic nerve activity measuring apparatus as claimed in claim 5, wherein
the pulse wave amplitude ratio includes the ratio between the P wave and the D wave.

7. The autonomic nerve activity measuring apparatus as claimed in claim 5, wherein
the pulse wave acceleration amplitude ratio includes the ratio between a b wave and a d wave.

8. The autonomic nerve activity measuring apparatus as claimed in claim 1, further comprising
a respiration detection unit, configured to detect a respiration signal from the living body,
wherein the electric stimulation unit applies the electric stimulation to the living body in response to the detected respiration signal.

9. The autonomic nerve activity measuring apparatus as claimed in claim 8, wherein
the respiration detection unit detects the respiration signal by using one of an airway flow sensor, a thermistor sensor, an airway pressure sensor, a carbon dioxide concentration sensor, an impedance sensor, and a photoplethysmographic sensor.

10. The autonomic nerve activity measuring apparatus as claimed in claim 8, wherein
the respiration signal includes at least one of expiration and inspiration.

11. The autonomic nerve activity measuring apparatus as claimed in claim 8, wherein
the electric stimulation unit applies the electric stimulation to the living body in either an expiratory phase or an inspiratory phase.

12. A method of measuring autonomic nerve activity of a living body, the method comprising:
applying electric stimulation to the living body by at least one electrode placed on the living body;
acquiring, by a sensor, at least two pulse wave signals from the living body, at least one of the pulse wave signals is derived from constriction of a peripheral blood vessel of the living body due to a nerve impulse induced by the electric stimulation; and
using a computer processor to carry out:
comparing the acquired pulse wave signals to produce a comparison result; and
determining abnormal response of an autonomic nerve based on the comparison result when no change occurs in the pulse wave signals.

13. The method as claimed in claim 12, wherein
the pulse wave signals, which are acquired before and after the electric stimulation is applied to the living body, are compared.

14. The method as claimed in claim 12, wherein
the electric stimulation includes a first electric stimulation and a second electric stimulation which are different from each other in intensity, and
the pulse wave signals, which are acquired when the first electric stimulation and the second electric stimulation are applied to the living body, are compared.

15. The method as claimed in claim 14, wherein
the first electric stimulation has low intensity, and
the second electric stimulation has high intensity.

16. The method as claimed in claim 12, wherein
the pulse wave signal is at least one of amplitude of a P wave, amplitude of a T wave, amplitude of a D wave, amplitude of pulse wave velocity, amplitude of pulse wave acceleration, a pulse wave amplitude ratio, a pulse wave velocity amplitude ratio, a pulse wave acceleration amplitude ratio, a power fluctuation pattern of each wavelength provided by pulse wave frequency analysis, and an elastic coefficient.

17. The method as claimed in claim 16, wherein
the pulse wave amplitude ratio includes the ratio between the P wave and the D wave.

18. The method as claimed in claim 16, wherein
the pulse wave acceleration amplitude ratio includes the ratio between a b wave and a d wave.

19. The method as claimed in claim 12, further comprising
detecting a respiration signal from the living body,
wherein the electric stimulation is applied to the living body in response to the detected respiration signal.

20. The method as claimed in claim 19, wherein
the respiration signal is detected by using one of an airway flow sensor, a thermistor sensor, an airway pressure sensor, a carbon dioxide concentration sensor, an impedance sensor, and a photoplethysmographic sensor.

21. The method as claimed in claim 19, wherein
the respiration signal includes at least one of expiration and inspiration.

22. The method as claimed in claim 19, wherein
the electric stimulation is applied to the living body in either an expiratory phase or an inspiratory phase.

* * * * *